United States Patent
Popov et al.

[11] Patent Number: 6,117,970
[45] Date of Patent: Sep. 12, 2000

[54] SODIUM SALT OF [POLY-(2,5-DIHYDROXYPHENYLENE)]-4-THIOSULPHURIC ACID OF LINEAR STRUCTURE AS REGULATOR OF CELL METABOLISM AND PRODUCTION METHOD THEREOF

[76] Inventors: Viktor Georgievich Popov, ul. Golubinskaya 7-2-292, I17574, Moscow; Ekaterina Mikhailovna Igumnova, ul. Priorova 30-3I, I25I30 Moscow, both of Russian Federation

[21] Appl. No.: 09/297,294
[22] PCT Filed: Oct. 28, 1997
[86] PCT No.: PCT/RU97/00338
§ 371 Date: Apr. 28, 1999
§ 102(e) Date: Apr. 28, 1999
[87] PCT Pub. No.: WO98/18758
PCT Pub. Date: May 7, 1998

[30] Foreign Application Priority Data

Oct. 30, 1996 [RU] Russian Federation ........... 96121039

[51] Int. Cl.$^7$ .................................................. C08G 2/18
[52] U.S. Cl. .................. 528/223; 528/220; 528/360; 528/361; 528/364; 528/499; 528/503
[58] Field of Search .................... 528/223, 220, 528/360, 361, 364, 499, 503

[56] References Cited

PUBLICATIONS

Chem Abstract 89:89881 "Reactions Between ρ–Benzoquinone or Potassium ρ–Benzoquinone Sulphonate and Sodium thiosulfate" Coops et al.

69:43210 "Kinetics of the reaction of ρ–Benzoquinone with Sodium Thiosulfate" Yoshiro et al.

No.: XP–002058125; title: Kinetics of the Reaction of ρ–Benzoquinone with Sodium Thiosulfate; Yoshiro Ogata, Yasuhiko Sawaki, an Sumio Gotoh; Jun. 19 1968;.

No.:XP–002058124; title: Paradontitis Treat After Surgical Intervening Sodium Poly P Di Hydroxy Phenylene Thiosulphate; Derwent; Sep. 17, 1990;.

No. XP–002058123; title: New Poly Hyroxy Phenylene Oligomer Helical Structure Useful Regulate Cell Energy System; Derwent; Sep. 12, 1995.

*Primary Examiner*—Duc Truong
*Attorney, Agent, or Firm*—Garrison & Associates PS; David L. Garrison

[57] ABSTRACT

Sodium salt of (poly-(2,5-dihydroxy-phenylene))-4-thiosulfonic acid, being a cyclo-linear polymer, is proposed as the regulator of a cell metabolism. There are provided for the production of the claimed preparation: interaction of para-benzoquinone and sodium thiosulfate at the molar ratio of 10:1 to 2:1, separation of a final product, and purification from admixtures. The interaction of para-bernzoquinone and sodium thiosulfate is made in a water-organic medium, preferably in the water-acetone one, at the temperature of 40 to 70 C.

11 Claims, 3 Drawing Sheets

SODIUM SALT OF [POLY-(2,5-DIHYDROXYPHENYLENE)]-4-THIOSULPHURIC ACID OF LINEAR STRUCTURE AS REGULATOR OF CELL METABOLISM AND PRODUCTION METHOD THEREOF

TECHNICAL FIELD

This invention relates to the field of a medicine and biology and concerns to preparations, regulating metabolism of a cell, which can be used for preventive maintenance and treatment of various diseases, as well as in the research purposes.

BACKGROUND ART

The majority of medicinal preparations, which are used now, are specific in the sense that their action is directed on elimination of the particular specific reasons and/or consequences of some pathological conditions.

However, there is a group of medicinal preparations of more general action, which biological activity is displayed in normalization of correct functioning of a live cell, breaking as a result of effect of adverse factors.

Among medicinal preparations permitted to medical application there is, for example, the group of therapeutic means, which render favorable influence on metabolic processes in a cell and display as a result the desired multifactor physiological effect [see, for example, M. D. Mashkovsky, "Medicinal Means" 11th ed., Moscow, "Medicine", 1988].

For example, cytochrome C accelerates a course of oxidizing processes; it is applied to improve of the tissue breath.

Adenosyne threephosphate influences actively general metabolism processes and consequently is widely applied to improve brain and coronary blood circulation.

Retabolyle and other anabolic steroids render positive influence on nitride exchange and moreover promote calcium fixation in bones.

Cerebrolysine, which represents a hydrolyzate of a brain substance, normalizes metabolism processes in the brain tissue; it is applied at breaks of central nervous system functions.

Ubiquinone normalizes the physiological condition of a cell in the state of hypoxya [see G. I. Andreeva "Influence of Ubiquinones and Their Analogues on Breath Circuit Ferments Activity", Microbiology, 1979, v.48, No.6, pp. 969–974].

The stacking-spiralized ortho-oligomer, containing hexacyclolinear nucleus, which quantity on a helix turn of a secondary structure of the oligomer is from 2.6 to 3, and having in the helix of the oligomer secondary structure more than 1, but less than 10 turns, is one of the most effective known preparations, capable to influence positively on a physiological condition of a cell.

An example of such stacking-spiralized ortho-oligomer, is the oligo-1,6-(2,5-dioxyphenilene)-thiosulfate of sodium.

Oligomers described above are the family of individual monomers, having benzol nucleuses in the structure in amount from 3 to 30.

The methods of separation of individual monomers and condition of a production of some or other monomers of a determined length and conventional purity are not described.

Standardization of the ready medicinal preparations is difficult in some extent under these circumstances.

Known substances dissolvable in water, spirit, acetone, but not dissolvable in the di/ethyl ether.

Oligomors of the similar structure have an ability to render regulating effect on functioning of bioenergetic systems of eukaryot and procaryot cells. See international application WO 96/08527 published on 21 Mar. 1996 (21.03.96), IPC C08G61/10, which is considered by the applicant as the nearest to his invention. A helix structure of the compound disclosed in that application and a stacking between turns of the helix were considered as characteristics which determine a biological activity of the compound.

A method of production of afore mentioned compound consists in that interaction is provided of para-benzoquinone and sodium thiosulfate in water-acetone medium at temperature not higher than 37 degrees, separation of the final product precipitation and deletion of impurities by di/etyl ether extraction.

All afore mentioned preparations have a spectrum of properties inherent to each of them, which determine a character of their practical application.

It is obvious from the state of the art that increase of means influencing on such fundamental properties of cells, as its metabolism is the actual target in the medicine and biology.

There are no routine ways for a search of substances with desired properties: finding of such substances relates to the inventive activity.

DISCLOSURE OF INVENTION

The objective of this invention is to broaden of a range of means, influencing on cells metabolism.

There was unexpectedly established as a result of research efforts by the applicant that the linear analogues of the known stacking-spiralized ortho-oligomers have the same biological activity as it was described previously for the spiral structure oligomers.

By other words, the linear oligomers of a similar chemical nature, but having no spiral configuration, appear capable to render regulating influence on cells metabolism.

In particular, the linear oligomer which have such ability is the oligo-1,6-(2,5-dioxy-phenilene)-thiosulfate of sodium, which applicant considers more correct to name hereinafter as the sodium salt of [poly-(2,5-dihydroxy-phenilene)]-4-thiosulfonic acid.

This linear polymer is a mixture of monomers, including compounds having from 2 to 6 benzol nucleuses.

There was no possibility to produce individual monomers—components of the polymer mixture of a satisfactory purity, but it is possible to produce the polymer mixture comprising preferably monomers of the required length by varying conditions of chemical synthesis of these compounds.

The molecular mass of the polymer compound can be in the limits from 352 to 784.

The compound is a powder of black colour with no smell, a little salted by taste.

It is easily dissolvable in water and practically not dissolvable in 95% of ethanol, aceton or diethyl ether.

It has no precise melting point temperature.

Extinction of 0.003% solution in water at the wavelength of 305 nm is 18.9 l/g*cm.

The ultraviolet spectrum shows brightly expressed maximum at the wavelength of 305±1 nm.

The place of the maximum does not change at change of the pH value in the range from 5.0 to 9.0, i.e. the hypso- and bathocromic effects are absent, that testifies for certain that the polymer does not contain spiral structures.

Absorption bands in infrared spectrum are in areas of 610–630 cm$^{-1}$, 790–810 cm$^{-1}$, 1195–1215 cm$^{-1}$, 1440–1460 cm$^{-1}$.

The polymer product shows expressed biological activity, displayed in respect of microorganisms, desegregated cells of a living tissue, animals and humans.

Its main direction of biological action is the normalization and optimization of living cells metabolism, especially in hypoxya conditions.

Other important feature of the proposed polymer is its property to increase the working ability of an organism.

A method of production of the sodium salt of [poly-(2,5-dihydroxy-phenilene)]-4-thiosulfonic acid consists in that interaction is provided of para-benzoquinone and sodium thiosulfate in organic solvent medium at temperature of 40 to 70° C., separation of the final product precipitation and purification by ethyl alcohol.

Interaction is preferably provided in water-aceton medium.

Thus, the claimed compound differs from the nearest known structural and functional analogue with similar biological activity by following features:

it has a linear and not a spiral configuration;

it is a mixture of monomers and not a separate individual monomer;

it is not dissolvable in spirits and acetone, in difference from the analogue;

it is produced by a method which parameters differ from the method of production of the analogue.

The method of production of the claimed compound has a distinction consisting in that the polymer synthesis is carried out at higher temperature, namely at the temperature of 40 to 70° C.

DETAILED DESCRIPTION OF THE INVENTION

The applicant has proven, by an experimentation, that the stacking-spiralized configuration of oligomers belonging to the row of oligo-1,6-(2,5-dioxyphenilene)-thiosulfate of sodium is not the necessary condition for biological activity, directed on normalization and optimization of live cell functions.

It was discovered, in particular, that the sodium salt of [poly-(2,5-dihydroxy-phenilene)]-4-thiosulfonic acid, which is the linear polymer, has the ability of positive influence on metabolism processes in a cell.

This result is not obvious, because it is known, that the molecule properties are defined by its space orientation and, in particular, the unique properties of nucleic acids are connected just with its particular three-dimensional space position.

It is quite correct, in this connection, to consider chemical compounds, characterized by its space structures, as separate individual substances.

The claimed polymer compound has the following structural formula:

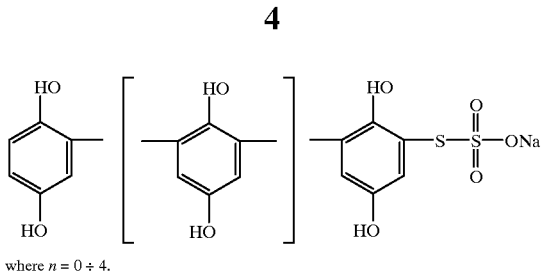

where $n = 0 \div 4$.

The polymer compound has the molecular mass in limits from 352to 784. The molecular formula of the compound is $NaS_2C_{12+6n}O_{7+2n}H_{10+4n}$.

The polymer is a mixture of separate monomers, it contains monomers with structure having from 2 to 6 benzol nucleuses.

The ratio of monomers in the polymeric product can differ, but, as it was shown in experiments, this ratio does not render decisive influence to a degree of biological activity of such preparation.

Nevertheless, it is possible to produce the polymeric product with the standard composition of monomers, if observing identical conditions.

Moreover, it is possible to synthesize the product with a different ratio of monomers by selection of the synthesis appropriate conditions.

Figure 1:
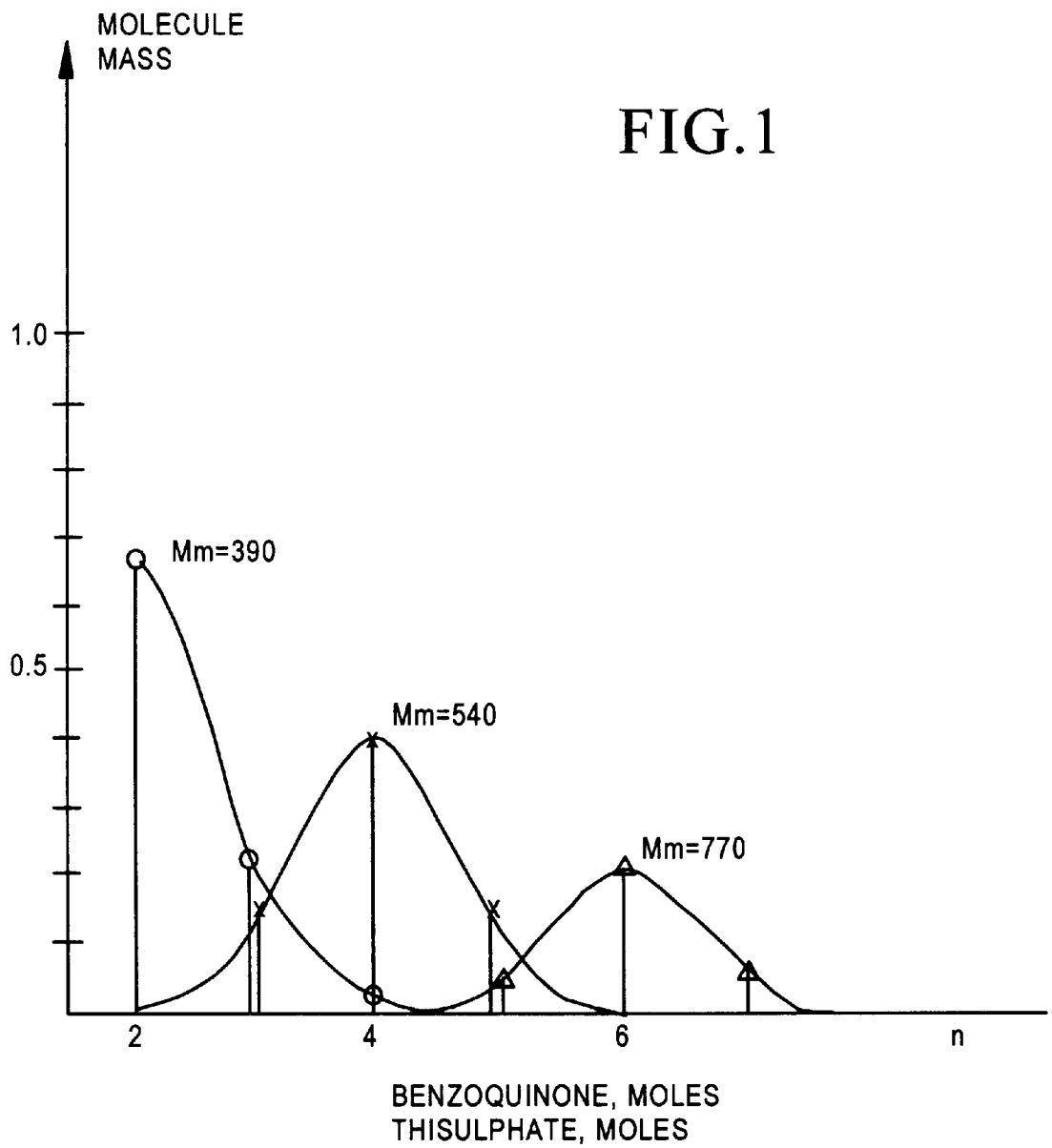
FIG. 1 represent a dependency of the produced polymeric product molecule mass on the initial products ratio.

FIG. 1 shows the general tendency of changes of produced polymeric product molecule mass versus the initial products ratio, which describes indirectly the monomer composition in he final mixture.

The compound is a powder of black colour with no smell, a little salted by taste.

It is easily dissolvable in water and practically not dissolvable in 95% of ethanol, aceton or diethyl ether.

It has no precise melting point temperature.

Extinction of 0.003% solution in water at the wavelength of 305 nm is 18.9 l/g*cm.

Figure 2:
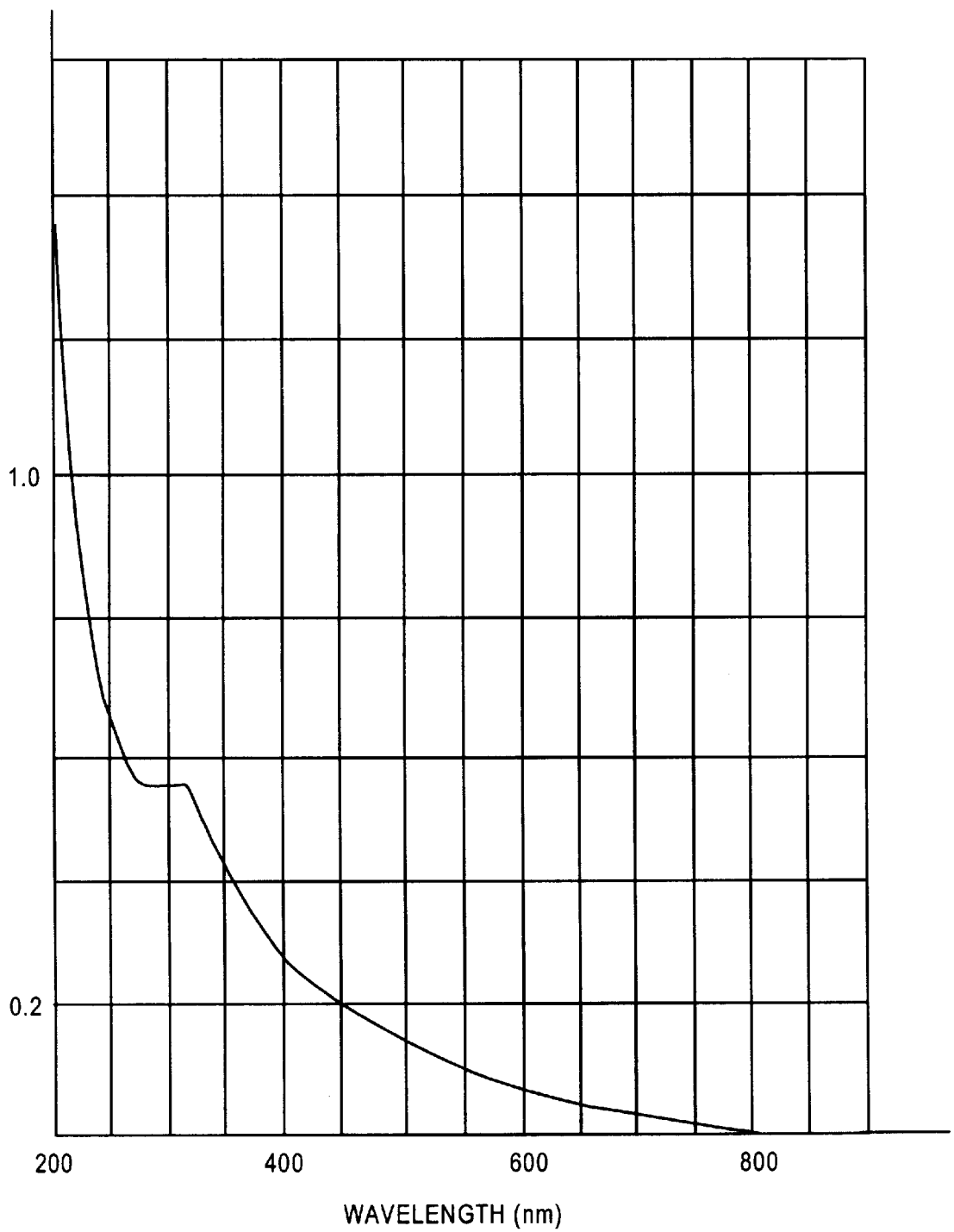
FIG. 2 shows the ultraviolet spectrum of the produced polymeric product.

The ultraviolet spectrum shows brightly expressed maximum at the wavelength of 305±1 nm (see FIG. 2).

The place of the maximum does not change at change of the pH value in the range from 5.0 to 9.0, i.e. the hypso- and bathochromic effects are absent, that testifies for certain that polymer does not contain spiral structures.

Figure 3:
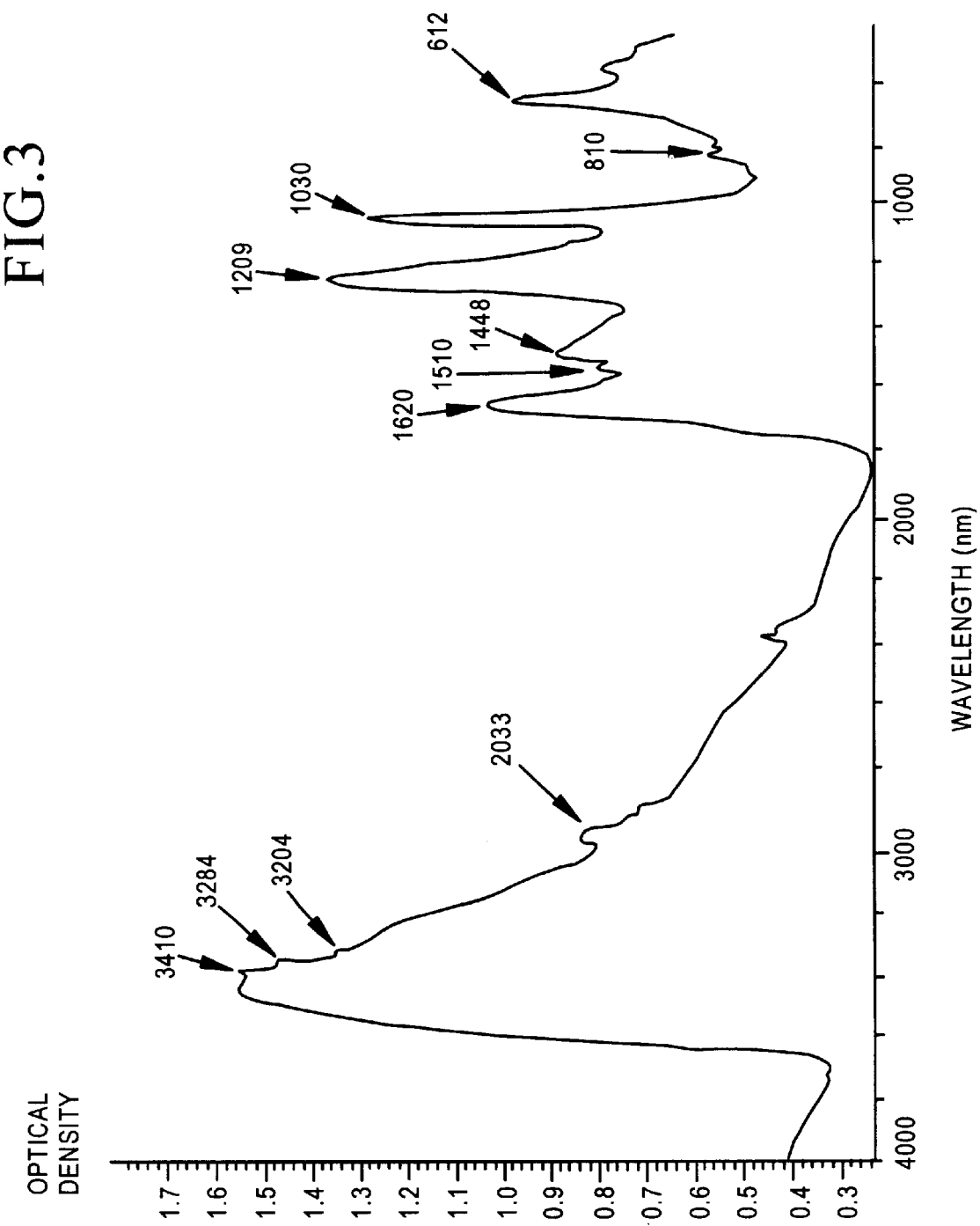
FIG. 3 shows the infrared spectrum of the produced polymeric product.

It is characterized by absorption bands in the infrared spectrum area of 610–630 cm$^{-1}$, caused by groups C—S and S—O valency oscillations; in the area of 790–810 cm$^{-1}$, caused by non-planar deformation oscillations of non-substituted hydrogen atoms in the benzol ring; in the area of 1195–1215 cm$^{-1}$, caused by deformation oscillations of C—OH in the aromatic ring; in the area of 1440–1460 cm$^{-1}$, caused by group C—S valency oscillations (See FIG. 3). The other bands of absorption, which appear in the spectrum, are not characteristic, they are overlapped by spectra of initial reaction products and were not identified.

The main basic difference of patented compound from its nearest analogue consists in that the known compound has a spiral structure, whereas the proposed compound has no spiral structure, it is the linear polymer.

The claimed compound is a mixture of monomers and the monomers in the mixture contains in its structure from 2 to 6 benzene nucleuses, whereas the known compound is a family of individual monomers containing from 3 to 30 benzol nucleuses.

Besides, the known and proposed compounds characterized by different solubility: in distinction of the known compound, the proposed one is not dissolvable in the spirits and aceton.

A biological activity of the proposed sodium salt of [poly-(2,5-dihydroxy-phenilene)]-4-thiosulfonic acid was studied on cells cultures, microorganisms, animals and human beings; some results are indicated below.

The whole complex of the applicant's experimentation results gives the basis for a conclusion that the claimed compound normalizes and optimizes the live cell metabolism for any tested organisms representing the various stages of evolution.

A visible side of favorable effect of the claimed compound on metabolism consists, in particular, in more active growth of desegregated cells of a live tissue, in greater microorganisms production activity, in increase of serviceability of the experimental animals, and in antihypoxy effect for the human beings.

Results of some tests of a claimed compound influence on viable biological objects are shown below.

All tests were made with the sodium salt of [poly-(2,5-dihydroxy-phenilene)]-4-thiosulfonic acid of the linear structure, containing about 60% of dimeric compound, if the other was not expressly stated below.

All tests were conducted by a classical method repeatedly described in the literature [See, for example, Pert S. D. Osnovy kultivirovania mikroorganizmov i kletok (Basics of microorganisms and cells cultivation), Moscow, Ed. "Mir", 1978].

It may be seen from this Table that the claimed preparation increases notably the cell proliferation activity and that this effect is retained for at least seven passages.

TABLE 1

Influence of the sodium salt of [poly-(2,5-dihydroxy-phenilene)]-4-thiosulfonic acid on cells BHK-21 growth

| Concentration of the preparation (Millions/ml) | Cells concentration, (Millions/ml) Passage | | | | | | | Average cells concentration (Millions/ml) |
|---|---|---|---|---|---|---|---|---|
| | 1 | 2 | 3 | 4 | 5 | 6 | 7 | |
| 0    | 1.8 | 1.3 | 1.5 | 1.3 | 1.7 | 1.5 | 1.5 | 1.5 |
| 2.5  | 1.9 | 2.0 | 1.7 | 1.7 | 2.1 | 1.8 | 1.9 | 1.9 |
| 5.0  | 2.1 | 1.7 | 1.8 | 2.0 | 1.9 | 1.9 | 1.8 | 1.9 |
| 10.0 | 1.7 | 1.8 | 1.6 | 1.9 | 2.0 | 1.7 | 1.9 | 1.8 |

The obtained results show that the sodium salt of [poly-(2,5-dihydroxy-phenilene)]-4-thiosulfonic acid stimulates growth of the isolated BHK-21 cells, increasing cells accumulation up to 25 percent approximately, without any toxic action of the tested substance up to its concentration of 10 mg/ml. This parameter is especially important, as far as just the isolated cells of living tissue are the most sensitive toxicity revealing test-system of all ones used for this purpose.

Revealing of stimulating action of the claimed compound at the microorganism level was made, in particular, by treatment of the commercial *Aspergillus niger* strain which is the producer of the citric acid. The preparation was added to the feeding medium for sowing only. As a result of a standard conditions experiment of commercial scale there was obtained an increase of the citric acid yield up to 21%, molasses economy up to 9%, and a reduction of the production cycle period up to 10%.

Some of the results which were obtained at experimentation are shown in following Table 2.

TABLE 2

Influence of the sodium salt of [poly-(2,5-dihydroxy-phenilene)]-4-thiosulfonic acid on biological syntheses of thecitric acid by the *Aspergillus niger* culture

| Index of production | Concentration of the sodium salt of [poly-(2,5-dihydroxy-phenilene)]-4-thiosulfonic acid in the medium for sowing, mg/ml | |
|---|---|---|
| | 0 | 10 |
| Maximum concentration of the citric acid, g/l | 9.2 | 11.2 |
| Percentage of the citric acid of the sum of acids | 69 | 72 |
| Average period of fermentation, days | 7 | 6.4 |

The standard determination technique of so called "swimming period", as described, for example, in the Methodical Recommendations for Experimental Study of Offered for Clinical Study Preparations as an Antihypoxya Means, approved by the Pharmacological Committee of the USSR Public Health Ministry at Apr. 11, 1990, Protocol No. 7, was used for evaluation of tested compound influence on a serviceability.

The proposed preparation was injected to the animals under test, to the mice in this case, then they were placed in a vessel with water, and the evaluation was made of their ability to be held up on the water surface. The ability was indicated by the free swimming period. Comparison was made with the mice having no preparation.

Some of the results obtained are shown in Table 3.

TABLE 3

Influence of the sodium salt of [poly-(2,5-dihydroxy-phenilene)]-4-thiosulfonic acid on the swimming period standard test for mice, minutes and seconds

| NoNo | Comparison group | Sample 1 | Sample 2 | Sample 3 |
|---|---|---|---|---|
| 1  | 8 00  | 18 20 | 9 10  | 18 20 |
| 2  | 8 20  | 24 30 | 21 00 | 17 55 |
| 3  | 8 30  | 26 30 | 21 25 | 20 00 |
| 4  | 9 00  | 28 00 | 22 10 | 22 00 |
| 5  | 9 20  | 29 05 | 22 20 | 23 00 |
| 6  | 9 55  | 30 02 | 27 00 | 23 20 |
| 7  | 10 10 | 30 05 | 29 30 | 24 00 |
| 8  | 10 25 | 39 15 | 30 10 | 25 10 |
| 9  | 10 30 | 40 10 | 31 00 | 25 20 |
| 10 | 11 20 | 41 30 | 33 00 | 29 20 |

Samples tested were the preparations of claimed compound with various proportions of individual monomers: Sample 1 contains more than 60% of dimer, Sample 2 contains about 50% of dimer, and Sample 3 contains less than 40% of dimer.

Animals under test were female mice of the BALB line.

It is clear from Table 3 that the proposed means increases essentially the mice immunity to physical burdens in the experimental conditions.

Following results were obtained from the tests on rats survivability in the experimental hypoxya conditions under influence of the sodium salt of [poly-(2,5-dihydroxy-phenilene)]-4-thiosulfonic acid. The tests were carried out according to techniques, described in the afore mentioned Methodical Recommendations.

TABLE 4

Comparative efficiency of the sodium salt of [poly-(2,5-dihydroxy-phenilene)]-4-thiosulfonic acid as an antihypoxydant

| Preparation | Doze, mg/kg of the mass | Hemorrhoidal shock [1]) Rates survivability, %% | Circulative hypoxya [2]) Survivability after: | |
|---|---|---|---|---|
| | | | $24^h$ %% | $48^h$ %% |
| Ubiquinone | 200 | 20 | 60 | 30 |
| Cytochrome | 10 | 30 | 60 | 40 |
| Known one | 30 | 70 | 80 | 70 |
| Proposed one | 30 | 75 | 80 | 75 |
| Control | — | 0 | 20 | 15 |

Notes to Table 4:
[1]) Rats survivability after 6 hours from the phlebototny;
[2]) Rats survivability after the bandage of carotids.

The known preparation was an individual stacking-spiralized monomer, namely, the sodium salt of [tetra-(2,5-dihydroxy-phenilene)-4-thiosulfonic acid, and the proposed one was the polymeric sodium salt of [poly-(2,5-dihydroxy-phenilene)]-4-thiosulfonic acid containing 50% of dimers.

The high effect of the proposed linear structure compound is obvious, it is not less than the effect, which is achieved by use of the stacking-spiralized structure monomer.

Clinical researches of the claimed compound have shown, that the claimed compound, in particular, can normalize a patient immunity status at various pathologies.

TABLE 5

Influence of the sodium salt of [poly-(2,5-dihydroxy-phenilene)]-4-thiosulfonic acid on iuonocytes functional activity:
(1) - before the preparation reception
(2) - after the preparation reception

| Groups of patients tested; (n is the number in the group) | Functionally active monocytes, percents | | Phagocytic monocytes, percents | |
|---|---|---|---|---|
| | (1) | (2) | (1) | (2) |
| Ferrous deficiency anaemia (n = 17) | 52.3 ± 2.9 | 62.7 ± 3.1 | 15.7 ± 1.0 | 27.3 ± 1.5 |
| B-pholious deficiency anaemia (n = 3) | 48.3 ± 3.6 | 54.7 ± 3.2 | 21.7 ± 2.1 | 33.3 ± 3.1 |
| Infection and allergy polyarthritis (n = 5) | 39.6 ± 3.2 | 56.4 ± 4.2 | 18.4 ± 1.0 | 24.8 ± 2.8 |
| Leukaphenia (n = 14) | 41.3 ± 2.1 | 56.5 ± 3.1 | 13.4 ± 3.4 | 32.6 ± 6.1 |
| Trombophenia (n = 3) | 54.2 ± 4.5 | 64.2 ± 3.6 | 15.3 ± 2.4 | 34.3 ± 3.5 |
| No diseases (n = 50) | 60.0 ± 2.5 | | 30.2 ± 2.5 | |

These results, being reliable statistically ($p < 0.05$), show the claimed preparation ability to activate the cells metabolism, to increase the animals immunity to stress overloads, to normalize the human being cells systems functioning.

The preparation has no cancerogenous or mutagenous properties. Toxicity of the preparation is low. It makes more than 1500 mg/kg of weight at intravenous injection to white mice, while an average effective therapeutic dosage makes about 30 mg/kg of weight.

It can be prepared in such conventional medicinal forms, as a solution, powders, tablet, ointments.

A method of production of the sodium salt of [poly-(2,5-dihydroxy-phenilene)]-4-thiosulfonic acid consists in that interaction is provided of para-benzoquinone and sodium thiosulfate in organic solvent medium at the temperature of 40 to 70° C., separation of the final product precipitation and purification by ethyl alcohol.

In the preferable mode of realization of the claimed method interaction is provided of the para-benzoquinone solution in acetone and sodium thiosulfate water solution at the temperature of 40 to 70° C., separation of the final product precipitation and purification by boiling ethyl alcohol.

The molar ratio of para-benzoquinone and sodium thiosulfate should be maintained in limits 10:1 to 2:1.

The method of production of the claimed product differs from the method of production of the nearest structural analogue by that reaction of interaction is carried out at higher temperature (namely, at the temperature of 40 to 70° C., while for the production of the known compound the temperature of interaction should not exceed 37 degrees, see Examples 5 and 6 of WO 96/08527), and by that the separation of impurities is made by extraction by spirits, and not by the diethyl ether.

The final product was washed by such organic solvent as the spirit for removal of unreacted substances and impurities.

The optimum initial concentration of para-benzoquinone in acetone makes usually 5–16%. The optimum initial concentration of sodium thiosulfate in water makes usually 20–30%.

The final product was normally washed 2–3 times by 5 volumes of the solvent.

In several experiments the preparation was obtained proceeding from hydroquinone which was oxidized by a known method, and then the formed para-benzoquinone was combined (without its intermediate separation) with the sodium thiosulfate.

A mixture of products, which is produced at interaction of para-benzoquinone and sodium thiosulfate, contains a various number of cyclolinear structures with 2 to 6 benzol rings. Content of this mixture can be various, it depends on interaction conditions—reagents ratio, temperature, duration of reaction and etc. Some data on this account are indicated below.

TABLE 6

Content of the product of interaction of para-benzoquinone and sodium thiosulfate depending on molar reagents ratio

| Ratio of reagents thiosulfate// para-benzoquinone | Molecular mass | Output of the product (in %% of para-benzoquinone) |
|---|---|---|
| 1:3 | 370 | 55 |
| 1:6 | 540 | 58 |
| 1:9 | 760 | 56 |

If the reaction of interaction is carried out at temperature 65–70 degrees during 2 hours, increase of a para-benzoquinone part in the reaction medium results in greater formation of relatively long chain monomers.

TABLE 7

Content of the product of interaction of para-benzoquinone and sodium thiosulfate depending on temperature of reaction

| Reaction temperature, degrees of centigrade | Molecular mass | Output of the product (in %% of para-benzoquinone) |
|---|---|---|
| 50 | 580 | 40 |
| 65 | 545 | 55 |
| 80 | 520 | 58 |

If the reaction of interaction is carried out at the constant ratio of para-benzoquinone and sodium thiosulfate of 6:1 during 2 hours, increase of the temperature results in shortening of a produced monomers length.

TABLE 8

Content of the product of interaction of para-benzoquinone and sodium thiosulfate depending on duration of reaction

| Duration of reaction, hours | Molecular mass | Output of the product (in %% of para-benzoquinone) |
|---|---|---|
| 1 | 530 | 38 |
| 2 | 540 | 56 |
| 3 | 570 | 57 |

It the reaction of interaction is carried out at the ratio of para-benzoquinone and sodium thiosulfate which is equal to 6:1 at the temperature of 65 degrees, increase of the reaction duration results in a parallel increase of the monomer circuit length.

Regularities illustrated by Tables 6 to 8 should be taken into account when syntesing polymers of desirable composition.

The following Examples, not limiting the invention, illustrate the essence of the proposal in more detail.

EXAMPLE 1

Stirred tank of 50 liters volume was loaded by 1 kg of para-benzoquinone and flooded by 19.6 liters of acetone. Resulted 5% solution was stirred for 10 to 15 minutes, then flooded by 0.765 kg sodium thiosulfate dissolved in 1.7 liters of distilled water. Thiosulfate:benzoquinone ratio is 1:3. The mixture was stirred during two hours, maintaining the temperature within the limits of 65 to 70 degrees. After completion of the reaction the mixture was cooled, the precipitation was separated, dried, and extracted by boiled ethyl alcohol during 24 hours. The final product was than dried.

An output of the final product was 0.55 kg.

The molecular mass, which was determined by the cryoscopic method, was equalled 370. Contents of the sulfur, which was determined by the element analysis, makes 19.2%.

The sodium thiosulfate and benzoquinone which were used in this and following Examples were commercially available products of the "pure" category.

EXAMPLE 2

Stirred tank of 50 liters volume was loaded by 1 kg of para-benzoquinone and flooded by 19.6 liters of acetone. Resulted 5% solution was stirred for 10 to 15 minutes, then flooded by 0.38 kg sodium thiosulfate dissolved in 0.9 liters of distilled water. Sodium thiosulfate:benzoquinone ratio is 1:6. The mixture was stirred during one hour, maintaining the temperature of 70 degrees. After completion of the reaction the mixture was cooled, the precipitation was separated, dried, and extracted by boiled ethyl alcohol during 24 hours. The final product was than dried.

An output of the final product was 0.50 kg.

The molecular mass, which was determined by the cryoscopic method, was equalled 540. Contents of the sulfur, which was determined by the element analysis, makes 14.5%.

EXAMPLE 3

Stirred tank of 50 liters volume was loaded by 1 kg of para-benzoquinone and flooded by 19.6 liters of acetone. Resulted 5% solution was stirred for 10 to 15 minutes, then flooded by 0.26 kg sodium thiosulfate dissolved in 0.6 liters of distilled water. Sodium thiosulfate:benzoquinone ratio is 1:9. The mixture was stirred during three hours, maintaining the temperature of 80 degrees. After completion of the reaction the mixture was cooled, the precipitation was separated, dried, and extracted by boiled ethyl alcohol during 24 hours. The final product was than dried.

An output of the final product was 0.55 kg.

The molecular mass, which was determined by the cryoscopic method, was equalled 740. Contents of the sulfur, which was determined by the element analysis, makes 11.3%.

INDUSTRIAL APPLICABILITY

This invention is industrially applicable in the medicine and biology, it can be used for preventive maintenance and treatment of various diseases, as well as in the research purposes.

The distinctions of the proposed method from the known one allows to obtain the product, distinguished from the known product.

The preparation according to this invention, at the best knowledge of the applicant, was not described earlier, and there are no information on its influence on the cell metabolism; the method of its production was not known earlier too.

The claimed compound had passed intensive clinical tests; it is permitted in established order in Russia to practical use in medical practice.

What is claimed is:

1. Sodium salt of [poly-(2,5-dihydroxy-phenilene)]-4-thiosulfonic acid of linear structure of general structural formula:

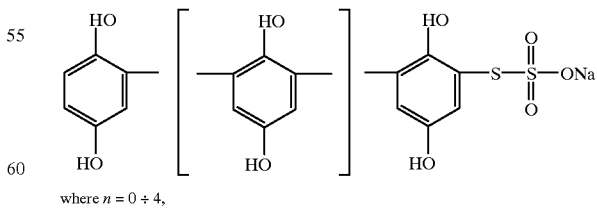

where $n = 0 \div 4$, as the regulator of a cell metabolism said compound having activity.

2. Method of production of the sodium salt of (poly-(2, 5-dihydroxy-phenilene))-4-thiosufonic acid of linear structure characterized by the following steps: interaction of an organic solvent solution of para-benzoquinone and an aqueous solution of sodium thiosulfate at the molar ratio of 10:1 to 2:1 and at the temperature of 40 to 70° C., separation of a final product from the reaction mixture, and purification from admixtures.

3. The compound of claim 1 formed by reacting para-benzoquinone with sodium thiosulfate in an organic solvent medium at 40 to 70° C. to form a precipitate and thereafter separating, drying and purifying said precipitate.

4. The compound of claim 1 having a molecular mass in the range of 352 to 784.

5. The method of claim 2 wherein said para-benzoquinone is present in an acetone solution to which an aqueous solution of sodium thiosulfate is added; the resulting admixture is maintained at a temperature in the range of about 65 to 70° C. for a period of about one to two hours.

6. The method of claim 5 wherein the ratio of sodium thiosulfate to benzoquinone is about 1:6.

7. The method of claim 2 wherein said para-benzoquinone is dissolved in acetone in a reaction vessel to which an aqueous solution of sodium thiosulfate is added.

8. The method of claim 7 wherein said acetone solution of para-benzoquinone contains about 5% para-benzoquinone.

9. The method of claim 2 wherein said sodium salt has a molecular weight in the range of about 352 to 784.

10. The method of claim 2 wherein said interaction is made by addition of the aqueous sodium thiosulfate solution to the organic solution of para-benzoquinone.

11. The method of claim 2 wherein said organic solvent is acetone.

* * * * *